Figure 1:
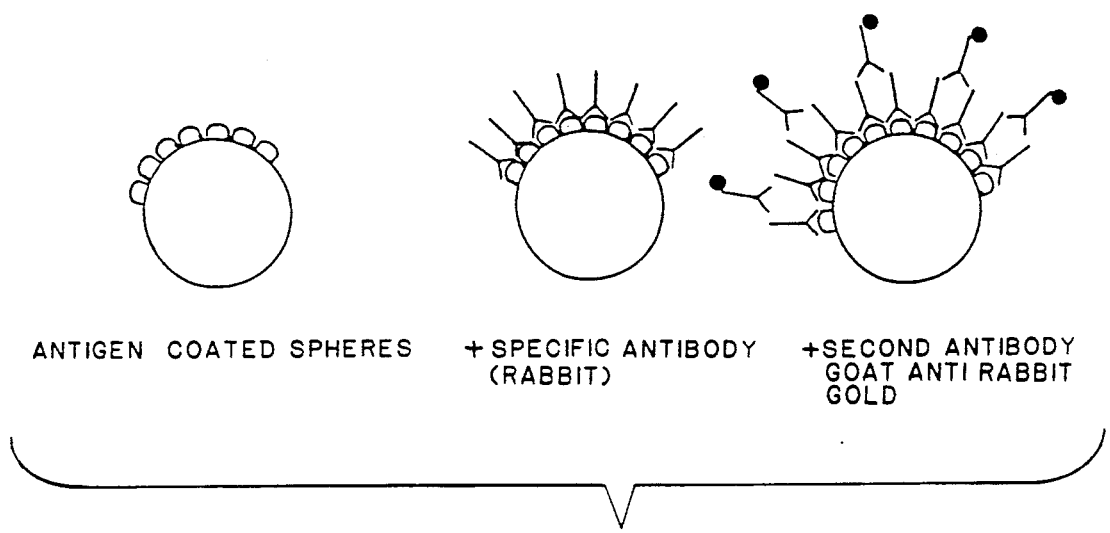

United States Patent [19]

Hari et al.

[11] Patent Number: 5,079,172
[45] Date of Patent: Jan. 7, 1992

[54] METHOD FOR DETECTING THE PRESENCE OF ANTIBODIES USING GOLD-LABELED ANTIBODIES AND TEST KIT

[75] Inventors: V. Hari, Bloomfield Hills; David A. Baunoch, Pontiac; Pritam Das, Detroit, all of Mich.

[73] Assignee: Board of Trustees operating Michigan State University, East Lansing, Mich.

[21] Appl. No.: 267,320

[22] Filed: Nov. 4, 1988

[51] Int. Cl.⁵ ................. G01N 33/543; G01N 33/545; G01N 33/553
[52] U.S. Cl. ........................................ 436/518; 435/5; 435/7.2; 435/7.33; 435/973; 435/975; 436/525; 436/531; 436/532; 436/533; 436/534; 436/801
[58] Field of Search ............... 436/501, 518, 524, 525, 436/538, 540, 801, 533, 534, 531, 532; 435/7, 7.95, 973, 5, 7.2, 7.33, 975; 424/3; 530/811

[56] References Cited

U.S. PATENT DOCUMENTS

| | | | |
|---|---|---|---|
| 4,313,734 | 2/1982 | Leuvering | 422/61 |
| 4,315,907 | 2/1982 | Fridlender et al. | 435/7.95 |
| 4,420,558 | 12/1983 | DeMey et al. | 435/7 |
| 4,446,238 | 5/1984 | DeMey et al. | 436/527 |
| 4,486,530 | 4/1984 | David et al. | 436/534 |
| 4,853,335 | 8/1984 | Olsen et al. | 436/525 |
| 4,859,612 | 8/1989 | Cole et al. | 436/525 |
| 4,879,213 | 11/1989 | Fox et al. | 435/7.95 |
| 4,879,220 | 11/1989 | Mrsny et al. | 436/526 |

FOREIGN PATENT DOCUMENTS

8331514  11/1983  United Kingdom .

OTHER PUBLICATIONS

Voller et al., Enzyme Immunoassays, Chap. 6, pp. 77-86, Alternative Immunoassays Ed. W. P. Collins, John Wiley & Sons, 1985.
Horisberger, Marc., "Colloidal Gold as a Tool in Molecular Biology", TIBS, Nov. 1983, pp. 395-397.
Engvall et al., Immunochemistry 8, 871 (1971).
Butler, J. E. et al., J. Immunol. Methods 20, 365 (1971).
Johannsson, A. et al., J. Immunol. Methods 87, 7 (1986).
Logtenberg, T. et al., Immunol. Lett. 9, 343 L9185).
Sedgwick, J. D. et al., J. Immunol. Methods 87, 37 (1986).
Kemeny, D. M. et al., Immunol. Today 7, 67 (1986).
Ljunggren, K. et al., J. Immunol. Methods 104 (1987).
Kimball, S. R. et al., J. Immunol. Methods 106, 217-223 (1988).
Moeremans, M. et al., J. Immunol. 74, 353-360 (1984).
Stiffler-Rosenberg et al., J. Clin. Microbiology, 8, 473 (1978).
Rembaum, A. et al., J. Science 208, 364 (1980).
Bourel, D. et al., J. Immunol. Methods 106, 161 (1988).
Fraenkel-Conrat, H., Virology, vol. 4, pp. 1-4 (1957).

Primary Examiner—David Saunders
Attorney, Agent, or Firm—Ian C. McLeod

[57] ABSTRACT

A method and test kit for detecting a first antibody using a gold particle labeled secondary antibody is described. Microspheres coated with an antigen reactive with the first antibody is reacted with the first antibody from serum or other sources. The gold-labeled antibody is reacted with the first antibody antigen complex on the microsphere and detected. Preferably the gold particles are detected using an electron microscope.

16 Claims, 5 Drawing Sheets

METHOD FOR DETECTING THE PRESENCE OF ANTIBODIES USING GOLD-LABELED ANTIBODIES AND TEST KIT

BACKGROUND OF THE INVENTION (1) Field of the Invention

The present invention relates to a method and test kit for detecting the presence of a detectable or first antibody in a sample using a gold-labeled second antibody to the first antibody and microspheres coated with an antigen reactive with the first antibody in a sandwich type assay method. In particular, the present invention relates to a method wherein an electron microscope is preferably used for the detection of the number of gold particles in the antigen-antibody complex on the microsphere which is related to the detectable antibody in the sample. The method is qualitative and can be quantitative.

(2) Prior Art

The detection of specific antibody in sera continues to be one of the surest ways of diagnosing autoimmune diseases and infections by various types of pathogenic agents. Solid phase immuno-assays based on enzyme-linked immunosorbent assays-ELISA (Engvall, E. and Perlman, P., Immunochemistry 8, 871 (1971) are among the most widely used techniques for detection of specific antibodies (Butler, J. E., et al. J. Immunol. Methods 20, 365 (1971); Johannsson, A., et al., J. Immunol. Methods 87, 7 (1986); Logtenberg, T., et al., Immunol. Lett. 9, 343 (1985); Sedgwich, J. D., et al., J. Immunol. Methods 87, 37 (1986); Kemeny, D. M. et al., Immunol. Today 7, 67 (1986); and Ljunggren, K., et al., J. Immunol. Methods 104 (1987)). Indeed, several improvements have been made to ELISA such that these techniques are fast replacing many isotopic (radiolabel) immunoassays (Kemeny, D. M., et al., Immunol. Today 7, 67 (1986)).

U.S. Pat. Nos. 4,420,558 and 4,446,238 to DeMey et al show the use of gold-labeled antibodies for detecting subtypes of blood cells or for localizing antigens in blood tissues. These methods are used for antigen detection rather than antibody detection. Examples of other related art in the use of gold-labeled antibodies is set forth in J. Immunol. Methods 106, 217-223 (1988) 74, 353-360 (1984); and GB No. 8331514 (831125).

The technique of coating spheres with specific antibodies for detection of cell surface and other antigens has been described by other investigators (Stiffler-Rosenberg, G. and Fey, H., J. Clin. Microbiology, 8, 473 (1978); Rembaum, A., and Dreyer, W. J., Science 208, 364 (1980); and Bourel, D., Rolland, A., LeVerge, R., and Genetet, B., J. Immunol. Methods 106, 161 (1988)). The problem is the visualization of the results.

OBJECTS

It is therefore an object of the present invention to provide a novel sandwich type assay method wherein a first antibody is detected using a second gold-labeled antibody. Further, it is an object of the present invention to provide a novel test kit which is easily used. Further, it is an object of the present invention to provide a method and test kit which is relatively simple and economical to produce. These and other objects will become increasingly apparent by reference to the following description and the drawings.

IN THE DRAWINGS

FIG. 1 illustrates the immunogold labeling procedure of the present invention used for detection of specific antibodies.

Figure 2A:
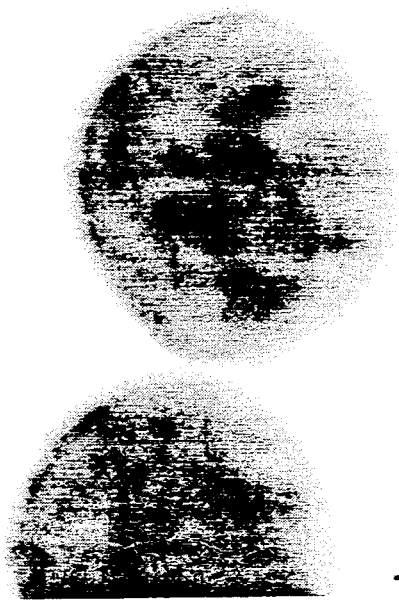
Figure 2B:
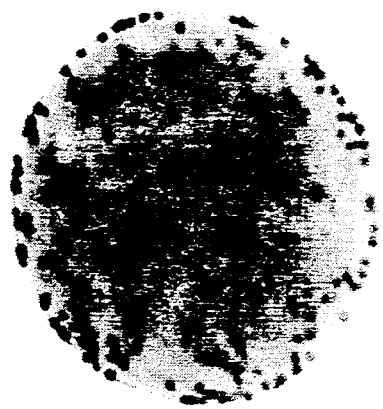
Figure 2C:
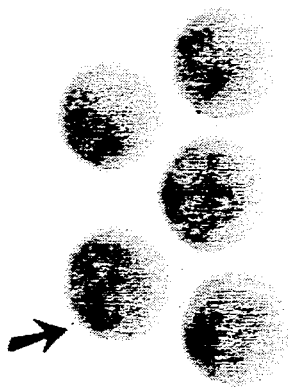
Figure 2D:

FIGS. 2A to 2D are electron microscope photographs showing immunogold labeling of spheres coated with tobacco etch virus (TEV) or tobacco mosaic virus (TMV) capsid proteins and exposed to normal or specific primary antibodies and then to gold-labeled secondary antibodies. FIG. 2A shows spheres (0.9 micrometers) coated with TEV-protein and incubated with normal preimmune serum followed by an attempt to bind with gold labeled secondary antibody. FIG. 2B is the same as in A but incubated with antiserum to TEV-capsid protein and then labeled with secondary gold conjugated antibody. FIG. 2C shows spheres (0.5 micrometers) coated with TMV protein and incubated with normal preimmune serum as in FIG. A. FIG. 2D is the same as in C but incubated with antiserum to TMV protein and then the gold labeled secondary antibody. The bar length equals 40 nm for A,B and 180 nm for C and D.

Figure 3A:
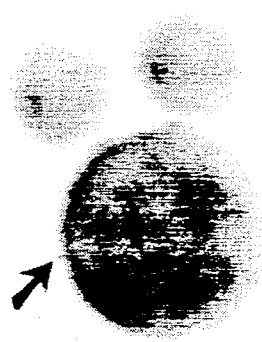
Figure 3D:
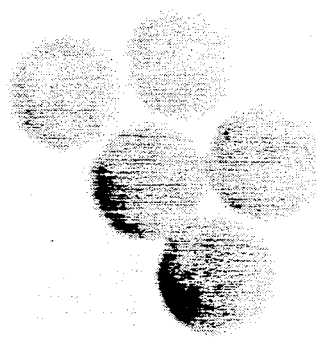
Figure 3B:
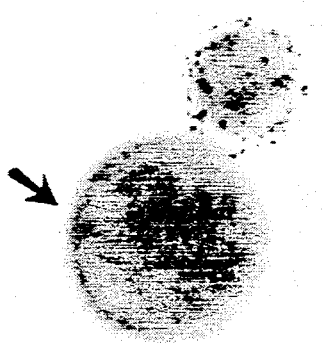
Figure 3E:
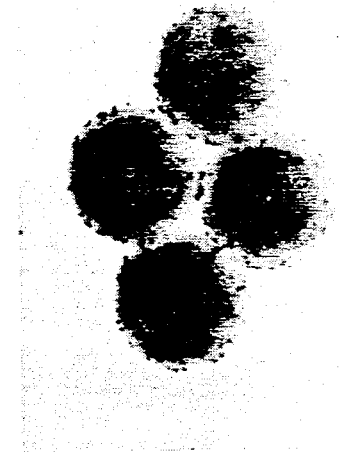
Figure 3C:
Figure 3F:
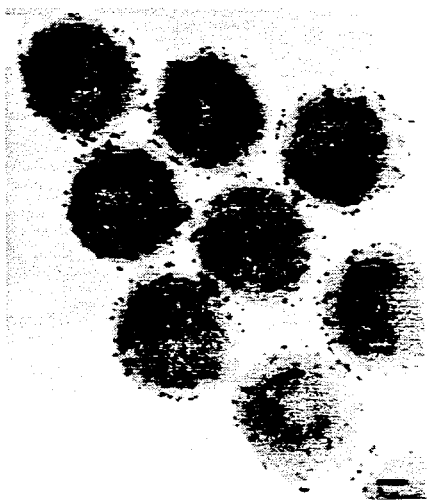

FIGS. 3A to 3C are electron microscope photographs showing the specificity of immunogold labeling when two different kinds of spheres coated with two different antigens are mixed and incubated with different primary sera. The spheres (0.9 micrometers) were coated with TEV-capsid protein and spheres (0.5 micrometers) coated with TMV-capsid protein were mixed and incubated with: in FIG. 3A normal serum showing no labeling of both large and small spheres, in FIG. 3B TMV-capsid antiserum showing labeling of the small TMV-coated spheres and in FIG. 3C, TEV-antiserum showing labeling of the large TEV-coated spheres only. FIGS. 3D,3E and 3F are electron microscope photographs showing that coating of the same spheres (0.5 micrometers).with two different antigens is possible. Spheres (0.5 micrometers) were coated with equimolar amounts of a mixture of TEV and TMV capsid proteins and were incubated with in FIG. 3D normal serum, in FIG. 3E TMV antiserum, and FIG. 3F TEV antiserum. The bar length equals 120 nm in all cases.

Figure 4A:
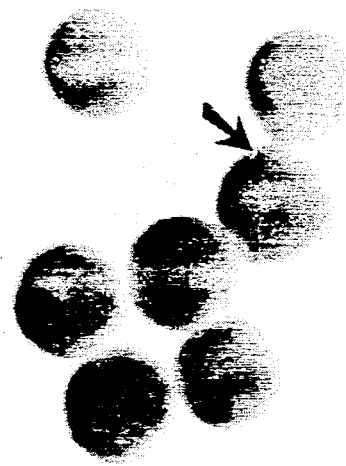
Figure 4B:
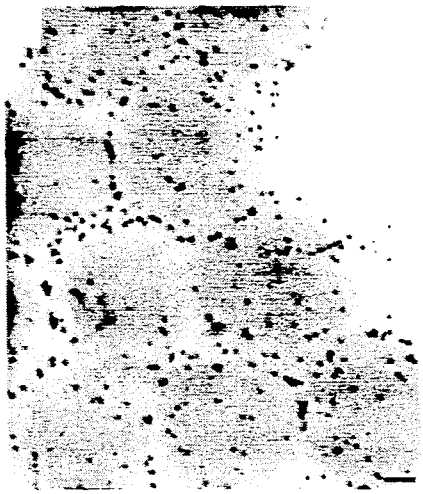
Figure 4C:
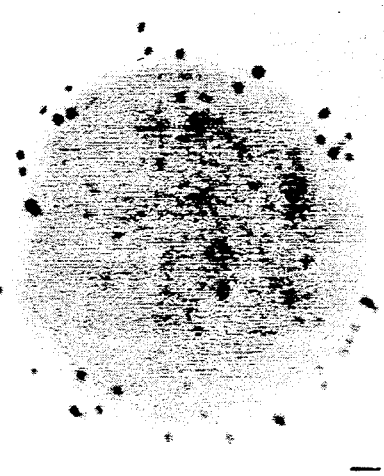
Figure 4D:
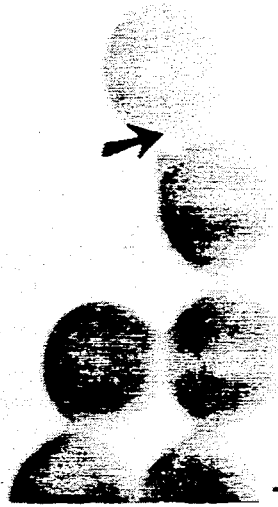
Figure 4E:
Figure 4F:
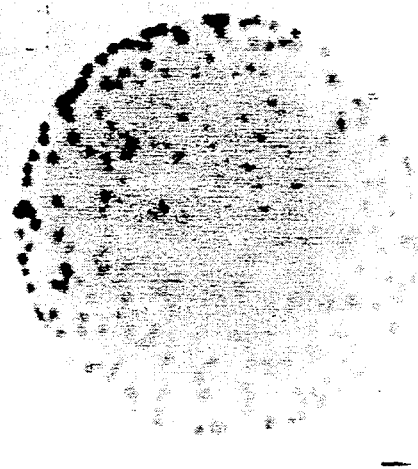

FIGS. 4A to 4F show electron microscope photographs of immunogold labeling of 0.5 micrometer spheres coated with staphylococcus enterotoxin B antigen (FIGS. 4A to 4C) or a cell lysate of Herpes simplex virus (FIGS. 4D to 4F). Spheres (0.5 micrometers) were coated with staphylococcus enterotoxin B antigen and incubated with: in FIG. 4A normal preimmune rabbit serum, in FIG. 4B Rabbit staphylococcus enterotoxin antiserum, and in FIG. 4C (enlargement of a sphere shown in FIG. 4B). Similarly spheres (0.5 micrometer) were also coated with a cell lysate containing Herpes simplex virus and incubated with: in FIG. 4D normal preimmune rabbit serum, in FIG. 4E specific polyclonal rabbit antiserum to HSV, and in FIG. 4F (enlargement of a sphere shown in FIG. 4E) showing the large number of gold particles. The length bar equals 120 nm for FIGS. 4A, 4B, 4D and 4E; 40 nm for FIG. 4C and 30 nm for FIG. 4F. In every case the reaction is specific.

Figure 5:
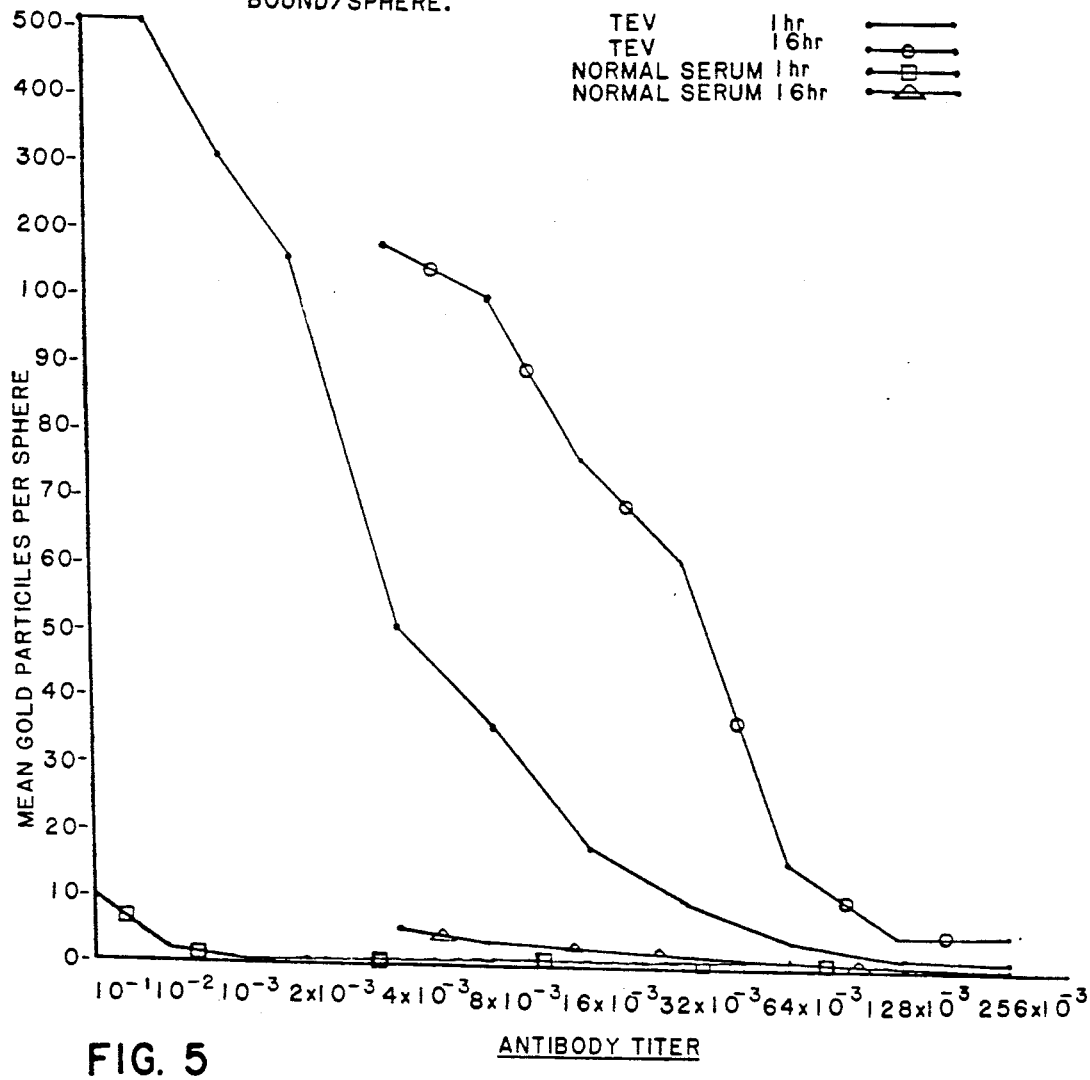

FIG. 5 is a graph showing the effect of antiserum dilution on the number of gold particles bound to spheres. Spheres (0.5 micrometers) were coated with TEV capsid protein and exposed to various dilutions of normal or TEV capsid rabbit antiserum for 1 hour or 16 hours before exposure to GAR-gold antiserum for 20 minutes. The number of gold particles on 50 spheres were counted at random and the mean/sphere calculated and plotted, (.—.) incubated with TEV, capsid serum for 1 hr, (.O.) incubated with TEV, capsid serum for 16 hours (.□.) incubated with normal rabbit antiserum for 1 hour, (.△.) incubated with normal rabbit antiserum for 16 hours.

GENERAL DESCRIPTION

The present invention relates to a method for detecting an antigen and first antibody complex in an assay which comprises: providing the antigen and first antibody complex on a surface with the antigen bound to the surface prior to forming the complex, wherein the first antibody is specific for the antigen; removing any excess unreacted first antibody from the antigen and first antibody complex; reacting the first antibody with a second antibody which complexes with the first antibody to form a second antibody, first antibody and antigen complex, wherein the second antibody is labeled with microscopically visible gold particles; removing any excess unreacted second antibody from the second antibody, first antibody and antigen complex; and detecting the number of gold particles in the second antibody, first antibody and antigen complex.

The present invention particularly relates to a method for detecting an antigen and first antibody complex in an assay which comprises: providing the antigen and first antibody complex on microspheres with the antigen bound to the microsphere prior to forming the complex, wherein the first antibody is specific for the antigen; removing any excess unreacted first antibody from the antigen and first antibody complex; reacting the first antibody with a second antibody which complexes with the first antibody to form a second antibody, first antibody and antigen complex, wherein the second antibody is labeled with microscopically visible gold particles; removing any excess unreacted second antibody from the second antibody, first antibody and antigen complex; and detecting the number of gold particles in the second antibody, first antibody and antigen complex.

Further the present invention relates to a test kit for detecting a first antibody in a fluid which comprises in separate container means: microspheres having an antigen which reacts with the first antibody bound to an exposed surface of the microsphere; and a second antibody which complexes with the first antibody wherein the second antibody is labeled with microscopically visible gold particles, wherein in use the first antibody in the fluid is complexed with the bound antigen and the second antibody is complexed with the first antibody and then the gold particles are detected. It is preferred to use electron microscope guides when the microspheres are to be examined with an electron microscope.

The method is diagrammatically illustrated in FIG. 1. Specific antigens are covalently linked to microspheres and these antigen-coated spheres are then incubated in antibody-containing solutions. Subsequently, the spheres are treated with immuno-gold labeled second antibody and preferably examined by transmission electron-microscopy. The labeling of antigen-coated spheres by the immuno-gold antibody indicates presence of specific antibody in the sera.

In order to develop the method a model system was used consisting of spheres coated with the capsid proteins of two plant viruses namely tobacco mosaic virus (TMV) and tobacco etch virus (TEV) for detection of antibodies specific to these proteins. Subsequently, the method was tested for detection of antibodies to staphylococcus enterotoxin B and Herpes simplex virus proteins by using spheres coated with these respective antigens. The method is applicable for detection of other types of antibodies, for instance, the Human Immunodeficiency Virus (HIV).

The protein binding microspheres can be obtained from a number of sources. They can be fluorescent or non-fluorescent when used with the preferred electron microscope method. In fluorescent detection methods, the microspheres should be non-fluorescent.

The spheres have surfaces containing various functional groups which react with the antigens. Included are amino, hydroxyl, aldehyde, epoxy, imidate, oxime or sulfhydryl or various active forms of these groups. Also binding can be achieved by electrostatic attraction. All of this is well known to those skilled in the art.

SPECIFIC DESCRIPTION

Capsid proteins of two plant viruses namely tobacco etch virus (TEV) and tobacco mosaic virus (TMV), as well as Staphylococcus enterotoxin B protein and proteins from a cell lysate containing Herpes simplex virus, were independently covalently bonded to microsphere particles. The antigen-linked spheres were then exposed to normal serum or antisera containing a specific antibody followed by treatment with gold-labeled secondary antibodies in a sandwich type assay. The spheres were then examined and photographed by transmission electron microscopy. The gold labeling of the spheres was specific and antibodies present in highly diluted antisera were detected.

Materials and Methods For Examples 1 to 5

Antigens and Antibodies

Dissociated virus capsid proteins from tobacco mosaic virus (TMV) and tobacco etch virus (TEV) were prepared by the acetic acid method (Fraenkel-Conrat, H., Virology, Vol. 4, pages 1 to 4 (1957)). The same method was used for preparing cell lysate proteins from VERO (African green monkey cells) cells infected with Herpes simplex virus (HSV). Staphylococcus enterotoxin B was purchased from Sigma Chemical Co., St. Louis, Mo.

Polyclonal antisera to TMV capsids and TEV capsids were prepared by injecting rabbits with dissociated virus proteins in the presence of Freunds incomplete adjuvant. Polyclonal antiserum to staphylococcus enterotoxin B was purchased from Sigma Chemical Co., St. Louis, Mo., and rabbit antiserum specific to Herpes simplex virus as well as HSV-infected VERO cells were obtained from Dr. Thomas Holland of the Immunology and Microbiology Dept. at Wayne State University, Detroit, Mich. and they are freely available from this source.

Covalent bonding of Microspheres with Antigens

Non-fluorescent protein reactive microspheres (MX-Covaspheres ®) of diameter 0.5 micrometers or 0.9 micrometers were purchased from Duke Scientific Corporation, Palo Alto, Calif. 94303. The binding is at amino groups of the protein. They were then coated with various antigens (TMV capsid protein, TEV capsid protein, staphylococcus enterotoxin B protein, cell lysate proteins from cells infected with Herpes Simplex Virus). A suspension 0.1 ml of the spheres containing approximately $1.1 \times 10^{11}$ spheres/ml (0.5 micrometer) or $3.3 \times 10^{10}$ spheres/ml (0.9 micrometer) were mixed after sonication with 20 micrograms of the antigen protein in water or 0.1M phosphate buffer pH 7.0 and after sonication for 2 minutes incubated at room temperature for 75 minutes. The mixture was then centrifuged in an Eppendorf microcentrifuge and the pellets containing the antigen-linked microspheres were resuspended in (Tris Buffered saline) buffer (0.1M Tris, 500 mM NaCl pH 7.5) containing 5% by wt/volume bovine serum albumin (BSA) BSA for 1 hour at room temperature. The BSA blocked any unreacted surfaces of the microspheres. After one more centrifugation at 10,000 for 10 min, the spheres were resuspended in the above buffer (TBS with 5% BSA) and stored at 4° C. before using.

Immunogold labeling

Ten microliters of antigen-coated spheres were loaded on Parlodion TM plastic film coated and then carbon coated 200 mesh nickel grids (3.05 micrometer) and excess liquid was drawn off with a filter paper. The coatings are standard in electron microscope techniques and are described in Practical Electron Microscopy For Biologists, John Wiley & Sons (1977) by Geoffrey Nicek and Biological Techniques for Transmission and Scanning Electron Microscopy, Ladd Research Industries, Inc. (1979) by Clinton J. Dawes. Other plastic films such as colloidion, Formfan TM can be used. The grids containing the sphere were treated with 0.1M Tris-buffered saline (TBS) pH 7.0 buffer containing 0.1% Tween-20 and 1% BSA wt/volume in order to block regions of the grid not containing spheres. The grids were then incubated for 1 hour with various dilutions of normal preimmune rabbit serum or rabbit specific antibody containing antiserum. After incubation, the grids were rinsed for 30 seconds with 0.1M Tris, 0.1% Tween-20 and 0.01% BSA, by wt/volume, (TTBS, Tris, Tween Buffered Saline), and immersed in the same buffer for 15 minutes. The process of rinsing and immersing in TTBS was continued three (3) times. After removing excess buffer, the grids were incubated for 20 minutes in a 1:25 dilution of goat anti-rabbit (GAR) IgG conjugated to 15 nm gold particles (Janssen Life Sciences Products located in Piscataway, N.J.). The incubated grids were washed by dipping three times with TTBS, dried, examined and photographed with a Philips 201 TM transmission electron microscope at 80 KV or 100 KV.

EXAMPLE 1

Immuno-labeling of TEV and TMV coated spheres

On an average, 0.9 micrometer spheres coated with TEV protein probed with normal serum showed an average of less than 1 gold particles per sphere (FIG. 2A) whereas, similar spheres treated with TEV antiserum had an average of more than 200 particles per sphere, (FIG. 2B). On the other hand, 0.5 micrometer spheres coated with TMV capsid protein were labeled with less than 1 gold particle per sphere when they had been exposed to normal serum (FIG. 2C) whereas comparable spheres treated with TMV antiserum showed an average of about 180 gold particles per sphere (FIG. 2D). In all cases, the gold particles on at least 50 spheres were counted for averaging purposes.

Nonspecific binding of the gold labeled secondary antibody to the antigen-coated spheres occurred if the blocking buffer after antigen coating did not contain adequate concentrations of BSA. Thus if spheres were resuspended in a blocking buffer containing only 0.01% BSA, then non-specific binding was significant. If however, the concentration of BSA during the blocking stop was increased to 5% and if the spheres were stored in buffer containing 5% BSA prior to primary and secondary antibody treatment, then the non-specific labeling was removed.

EXAMPLE 2

In order to further verify the specificity of the reaction, the large sized (0.9 micrometer) TEV-capsid coated spheres were mixed in approximately equal proportions with the smaller (0.5 micrometer) TMV-capsid coated spheres and then probed with normal, TEV or TMV antisera before exposure to secondary antibody (FIGS. 3A-C). The immunolabeling was highly specific with TMV antiserum labeling only the smaller TMV-coated spheres (FIG. 3B) and TEV antiserum labeling only the large TEV-coated spheres (FIG. 3C). Table I summarizes the actual counts of gold particles.

TABLE I

Concentration of Gold Particles Binding to Antigen-Linked Spheres*

| Primary Serum Tested | Avg. No. of Gold Particles Per Sphere Based on 50 Spheres | |
|---|---|---|
| | 0.9 μm TEV Spheres | 0.5 μm TMV Spheres |
| Normal Serum | 0.8 | 0.94 |
| TEV Antiserum | 151.1 | 0.86 |
| TMV Antiserum | 0.71 | 179.6 |

*Large 0.9 μm TEV-coated spheres and small (0.5 μm) TMV-coated spheres were mixed and exposed to normal, TEV-antiserum or TMV antiserum before immunolabeling.

EXAMPLE 3

Immunolabeling of spheres coated with two different antigens

The capacity and efficacy of immunolabeling of the same spheres coated with two different antigens was tested by coating 0.5 micrometer spheres with equimolar amounts, of TEV and TMV capsid proteins. Thus, spheres were coated with a solution containing equimolar amounts of TEV and TMV and then subjected to immunolabeling with normal, TEV or TMV antisera. As shown in FIGS. 3D-F normal serum did not react with the spheres whereas both TEV and TMV sera labeled the spheres. This showed that a mixture of antigens could be used to coat spheres and then be used to test for presence of two specific antibodies.

EXAMPLE 4

Immunodetection of antibodies to Staphylococcus B enterotoxin and Herpes simplex virus Microspheres (0.5 micrometer) coated with purified staphylococcus B enterotoxin protein (FIGS. 4A, B, C) or a cell lysate of cells infected with Herpes simplex virus (FIGS. 4D, E, F) were exposed to specific antisera prepared against purified staphylococcus enterotoxin proteins or Herpes simplex virus. In both cases, the labeling was specific and the respective antigens were detected by the respective antisera (FIGS. 4A-F).

EXAMPLE 5

Sensitivity of the labeling technique

Microspheres coated with TEV-capsid protein were probed with different dilutions of the normal preimmune serum or TEV-specific antisera and the number of gold particles binding to the spheres at various dilutions were counted (FIG. 5). The results are shown in Table II.

TABLE II

Immunogold labeling of spheres as a function of antibody dilution and time. Total number of gold particles per fifty spheres

| Antibody | TEV Serum | | Normal Serum | |
| --- | --- | --- | --- | --- |
| Dilution | 1 hour | 16 hour | 1 hour | 16 hour |
| 1:10 | 25,904 | — | 579 | — |
| 1:100 | 25,702 | — | 138 | — |
| 1:1,000 | 15,106 | — | 120 | — |
| 1:2,000 | 7,936 | — | 36 | — |
| 1:4,000 | 2,542 | 8,360 | 9 | 271 |
| 1:8,000 | 1,721 | 4,884 | 14 | 210 |
| 1:16,000 | 789 | 3,751 | 6 | 76 |
| 1:32,000 | 418 | 3,024 | 1 | 47 |
| 1:64,000 | 217 | 684 | 1 | 16 |
| 1:128,000 | 115 | 318 | 1 | 11 |
| 1:256,000 | 69 | 228 | 0 | 7 |
| 1:512,000 | 32 | 75 | 1 | 4 |
| 1:1,024,000 | 29 | 36 | 1 | 2 |

Table II shows the effect of antiserum dilution on the number of gold particles bound to the spheres. Spheres (0.5 um) were coated with TEV capsid protein and exposed to various dilutions of normal or TEV capsid rabbit antiserum for 1 hour or 16 hours before exposure to GAR-gold antiserum for 20 minutes. Fifty spheres were selected at random and the total number of gold particles observed was recorded.

As shown in FIG. 5, some non-specific binding occurred when spheres were exposed to normal serum diluted 1:10 but even this was negligible when compared to a 1:10 dilution of TEV antisera. Thus the 1:10 dilution of normal serum showed about 11 particles/sphere whereas the ones treated with specific antiserum showed about 518 particles/sphere. The method is able to detect antibodies at very high dilutions as shown in FIG. 5.

In order to determine if the sensitivity of the technique can be further improved so that greater binding of gold particles occurred even at very high antibody dilutions, the microspheres were incubated for 16 hours instead of 1 hour in primary antibody at various dilutions before exposure to secondary antibody. In this case, there was a noticeable increase in the number of gold particles bound to the spheres as shown in FIG. 5. Thus, for example, the number of particles bound to the spheres increased to 14 at 16 hours incubation as compared to 4 particles per sphere after 1 hour incubation with TEV antiserum at an antibody dilution of 1/64,000, whereas normal serum samples at the same dilution showed 0.02 particles/sphere at 1 hour and 0.32 particles/sphere at 16 hours incubation. Thus, the sensitivity of the technique can be increased by longer incubations with the first or primary antibody.

The gold particles preferably have a particle size between about 5 and 20 nanometers for use with an electron microscope. Larger or smaller gold particles of any size can be used both for electron microscopy and visual observation with a conventional microscope. The microspheres have a preferred diameter between about 0.1 and 10 microns for use with an electron microscope. For visualization by means of fluorescence or colorimetry on a light microscope, particles having a diameter between 5 and 5000 microns can be used. Other surfaces can be used, such as a flat surface or irregularly shaped particles; however, these are not preferred.

The second antibody which is gold particle labeled is reactive with the first antibody and is preferably a goat anti-rabbit IgG antibody or other antibody which reacts with the primary or first antibody to be detected. The gold labeled antibody does not have to be specific for a particular first antibody since there are usually no other interfering antibodies in the method and test kit. Examples of antibodies which are useful are human primary antibodies followed by anti-human secondary antibodies developed in rabbits, mice, goats or any other animal. Similarly the first antibodies can be from any animal so long as the gold conjugated second antibody recognizes the first antibody bound to the specific antigen on the spheres.

The spheres resuspended in solution are placed on the coated metal grid and the sides on the grid not covered by the spheres are blocked by using a protein such as BSA. Other proteins such as low fat milk powder can be used as a blocking agent.

Since the preferred method depends on actual indirect visualization of the antibody molecules rather than on colorimetric methods, false positives are eliminated. Further, because of the sensitive nature of this method, samples containing low specific antibody concentrations can be identified.

The method can be modified for light and fluorescence microscopy by using larger spheres combined with colorimetric and fluorescence methods currently used in standard or modified ELISA techniques. Further, commercially available computerized electron microscope imaging systems can be used for video recording and digital analysis of the gold particles on the spheres.

It is intended that the foregoing description be only illustrative of the present invention and that the present invention be limited only by the hereinafter appended claims.

We claim:

1. A method for detecting a first antibody complex in an assay which comprises:
    (a) providing an antigen bound to particles providing an assay support having a diameter between about 0.1 and 5000 microns, wherein portions of the assay support not bound to antigen are blocked with a non-antibody reactive protein;
    (b) reacting the antigen on the support with a first antibody wherein the first antibody is specific for the antigen to form an antigen and first antibody complex;
    (c) removing any excess unreacted first antibody from the antigen and first antibody complex;
    (d) reacting the first antibody with a second antibody which complexes with the first antibody to form a second antibody, first antibody and antigen complex, wherein the second antibody is labeled with microscopically visible gold particles;
    (e) removing any excess unreacted second antibody from the second antibody, first antibody and antigen complex; and
    (f) detecting the number of gold particles in the second antibody, first antibody and antigen complex with a microscope means;

(g) relating the number of gold particles to an amount of the first antibody.

2. The method of claim 1 wherein the microscope means is an electron microscope.

3. The method of claim 1 wherein the gold particles have an average particle size between about 5 and 20 nanometers.

4. A method for detecting a first antibody in an assay which comprises:
   (a) providing an antigen bound to a surface of a microsphere having a diameter of between about 0.1 and 5000 microns wherein portions of the surface not bound to are blocked with a non-antibody reactive protein;
   (b) reacting the antigen with a first antibody, wherein the first antibody is specific for the antigen, on the surface of the microspheres to form an antigen and first antibody complex;
   (c) removing any excess unreacted first antibody from the antigen and first antibody complex;
   (d) reacting the first antibody with a second antibody which complexes with the first antibody to form a second antibody, first antibody and antigen complex, wherein the second antibody is labeled with microscopically visible gold particles;
   (e) removing any excess unreacted second antibody from the second antibody, first antibody and antigen complex;
   (f) detecting the number of gold particles in the second antibody, first antibody and antigen complex with a microscope means; and
   (g) relating the number of gold particles to an amount of the first antibody.

5. The method of claim 4 wherein the microscope means is an electron microscope.

6. The method of claim 4 wherein the gold particles have an average particle size between about 5 and 20 nanometers.

7. The method of claim 4 wherein the microspheres are provided on an electron microscope grid means and the gold particles are detected with an electron microscope.

8. The method of claim 7 wherein the microspheres are complexed with the second antibody and washed to remove any second antibody which is not part of the first antibody, second antibody and antigen complex and then the gold particles are detected with the electron microscope means.

9. The method of claim 8 wherein the grid means has been treated so as not to react with the first or second antibody.

10. The method of claim 9 wherein the grid means is treated with a protein.

11. The method of claim 10 wherein the protein is bovine serum albumin.

12. The method of claim 4 wherein more than one antigen is provided on each microsphere.

13. The method of claim 4 wherein the second antibody is reacted with the first antibody over a period of at least one hour.

14. A test kit for detecting a first antibody in a fluid which comprises in separate container means:
    (a) microspheres having a diameter between about 0.1 and 5000 microns having an antigen which reacts with the first antibody bound to an exposed surface of the microsphere; and
    (b) a second antibody which complexes with the first antibody wherein the second antibody is labeled with microscopically visible gold particles, wherein in use the first antibody in the fluid is complexed with the bound antigen and the second antibody is complexed with the first antibody and then the gold particles are detected.

15. The test kit of claim 14 wherein the gold particles have an average particle size between about 5 and 20 nanometers.

16. The test kit of claim 14 wherein a protein is provided in the test kit for treating the grid means to block reaction of the grid means with the first or second antibody.

* * * * *

UNITED STATES PATENT AND TRADEMARK OFFICE
CERTIFICATE OF CORRECTION

PATENT NO. : 5,079,172
DATED : January 7, 1992
INVENTOR(S) : V. Hari, David A. Baunoch, and Pritam Das It is certified that error appears in the above-identified patent and that said Letters Patent is hereby corrected as shown below:

Title Page, [73] Assignee: "Board of Trustees, operating Michigan State University, East Lansing, Michigan", should be deleted, and "The Board of Governors of Wayne State University, Detroit, Michigan" should be inserted.

Title Page, [56] references Cited, after 4,853,335, "8/1984" should be deleted and "8/1989" should be inserted.

Title Page, Column 2, "Logtenberg, T. et al., Immunol. Lett. 9, 343 L9185)" should read "Logtenberg, T. et al., Immunol. Lett. 9, 343 (1985)--.

Column 2, line 38, delete the period "." after "micrometers)".

Column 2, line 41 "with in" should be --within--.

Column 10, line 33, Claim 14, after "detected" and before the period, the following should be inserted --and a number of the gold particles related to an amount of the first antibody; and (c) an electron microscope grid means for

UNITED STATES PATENT AND TRADEMARK OFFICE
CERTIFICATE OF CORRECTION

PATENT NO. : 5,079,172

DATED : January 7, 1992

INVENTOR(S) : V. Hari, David A. Baunoch, and Pritam Das

It is certified that error appears in the above-identified patent and that said Letters Patent is hereby corrected as shown below:

Continued:

supporting the microspheres in the assay--

Signed and Sealed this

Seventeenth Day of March, 1992

Attest:

HARRY F. MANBECK, JR.

*Attesting Officer*      *Commissioner of Patents and Trademarks*